United States Patent [19]

Farin

[11] Patent Number: 4,909,255

[45] Date of Patent: Mar. 20, 1990

[54] APPARATUS FOR ELECTRIC STIMULATION THERAPY EQUIPMENT

[75] Inventor: Günter Farin, Tübingen, Fed. Rep. of Germany

[73] Assignee: Erbe Elektromedizin GmbH, Tubingen, Fed. Rep. of Germany

[21] Appl. No.: 247,452

[22] Filed: Sep. 21, 1988

[30] Foreign Application Priority Data

Sep. 22, 1987 [DE] Fed. Rep. of Germany ....... 3731827

[51] Int. Cl.[4] ............................................. A61N 1/36
[52] U.S. Cl. ................................................ 128/420 A
[58] Field of Search .................. 128/420 A, 421, 422, 128/423

[56] References Cited

U.S. PATENT DOCUMENTS 4,071,033 1/1978 Nawracaj et al. ............... 128/420 A
4,280,504 7/1981 Rodler ............................ 128/420 A

FOREIGN PATENT DOCUMENTS

1109280 6/1961 Fed. Rep. of Germany.
1764672 7/1973 Fed. Rep. of Germany.

Primary Examiner—Lee S. Cohen
Assistant Examiner—Scott M. Getzow
Attorney, Agent, or Firm—Frishauf, Holtz, Goodman & Woodward

[57] ABSTRACT

In an electric stimulation therapy equipment two or more stimulation current circuits for simultaneous treatment of a patient, for example for muscle training or retraining, the two stimulation circuits have individual modulators for varying the intensity of the stimulation current and a function generator is provided for producing modulation in a cyclical pattern. The function generator also delivers pulses at a defined stage of the modulation cycle which go through a frequency divider with an adjustment for determining if, and by how much, the pulses are to be counted down. The frequency divider output is converted to provide control voltages for the two amplitude modulators for oppositely switching over the amplitude modulators into alternate modes. In the case of an interference current therapy equipment, the function generator controls cycles of phase modulation which produce cycles of relative phase between alternating currents supplied respectively to the two amplitude modulators and the frequency divider outputs alternately reduce the amplitude of one of the two modulators while the other of the two has an unreduced amplitude. In the case of a medium frequency stimulation therapy equipment the continuous output of the function generator provides both modulators with a voltage for producing cycles for stimulation for the patient's tissues and the frequency divider output alternately switches off the output of each modulated in turn while the other supplies modulator periods of medium frequency electric stimulation voltage.

10 Claims, 9 Drawing Sheets

APPARATUS FOR ELECTRIC STIMULATION THERAPY EQUIPMENT

This invention concerns apparatus for incorporation in electric stimulation therapy equipment in which at least two electric current circuits may be used simultaneously in the treatment of a patient.

Electric stimulation therapy equipment with two simultaneously usable electric stimulation circuits have been known for at least twenty years. One kind of electric stimulation therapy equipment in this class, for example, comprises electric stimulation equipment for electrical interference therapy. Such an equipment is described in German published patent application (AS) 1 109 280. A further development of the electric stimulation equipment described there is described in German Pat. No. 1 764 672. Furthermore, electric stimulation therapy equipment with at least two current circuits simultaneously applicable to the same patient are known in which each electrical circuit delivers direct currents or medium frequency alternating currents which can be modulated in amplitude to any desired extent.

The use of electric stimulation therapy equipment with two or more electrical circuits connected to the same patient, especially for muscle training, has long been subject to a serious problem arising from the fact that the time-wise coordination to each other of the stimulation effects of the respective circuits is not satisfactorily accomplished in the known electric stimulation therapy equipments. Thus, for example, in all interference current therapy equipments which are designed in accordance with German Pat. 1 764 672, no coordination in time is produced between the amplitude modulation occurring by interference in biological tissues by the vector sum of currents in the two circuits and, on the other hand, the additional amplitude modulation which is generated by a rhythmic current strength change directed more or less oppositely in the two or more current circuits. In consequence completely uncontrollable stimulation fluctuations occur in biological tissues, because in addition to the intended interference frequency produced by vectorial addition of the two or more currents that are not modulated in amplitude, an additional interference frequency in excited which results from the intended interference frequency and the rythmic amplitude modulation. The stimulation effects in the biological tissue proceeds almost chaotically when the intended interference frequency does not remain constant during the treatment, but additionally runs through some arbitrarily chosen interference frequency interval at a different speed or operates on a spectrum cycle Within the last ten years more and more so called medium frequency therapy equipments have become known which likewise are equipped with two or more electric circuits for simultaneous application to a patient. In these equipments the medium frequency alternating currents are premodulated in their amplitude in accordance with the intended stimulation effect. The modulation frequency, which determines the effect frequency in biological tissues, for example the frequency of muscle contractions, can be so adjusted in the known equipments of this kind, that they either remain constant during the entire duration of treatment or as above-described with respect to the known interference of current therapy equipment, run cyclically through a frequency interval or a frequency spectrum, at an adjustable speed. These medium frequency therapy equipments have been more and more preferred over the interference current therapy equipment because, by virtue of the unambiquous modulation frequency, the course of the stimulation treatment can be better controlled. Even with the use of the medium frequency therapy equipments, especially for muscle training, the problem still remains that a physiologically compatible stimulation is not possible in so far as in each case only direct acting (agonist) muscle, for example an inflecting or other contracting muscle, or one counteracting (antagonist) muscle, for example, a stretching muscles, can be treated.

The above-mentioned problems also arise in the case of low frequency therapy equipment, high voltage therapy equipment and pulse current therapy equipment, as soon as these are provided with two or more electric current circuits for simultaneous application to a patient.

Electric stimulation therapy equipment with two or more stimulation circuits simultaneously applicable to a patient is also knowm, for example the "Myocare" equipment, Model No. 6295 sold under the trademark "3M", in which the intensity of the stimulation currents in the individual stimulation current circuits can be alternatingly switched in and out. In this instance the various electric current perameters, such as amplitude, current flow duration, pause duration and rise and fall speed of the stimulation currents can be adjusted independently of each other. This equipment and technology, however, does not lend itself to the improvement of interference current therapy equipment. Moreover, in known stimulation current therapy equipment with two or more current circuits simultaneously applicable to a patient, the number of stimulation effects per unit of time cannot automatically be changed. It is for example desirable to have the number of stimulations changed from 5 to 10 and back to 5 during a certain interval duration and to repeat this interval cyclically during the overall treatment period.

SUMMARY OF THE INVENTION

It is an object of the invention to coordinate the stimulation effect of the individual current circuits with each other in electric stimulation therapy in which two or more stimulation current circuits are used for the same patient simultaneously so that the overall course stimulation is only slightly physiologically tiring for the tissue structures treated, or not tiring at all.

The invention is based on the recognition that stimulation treatment, especially in the case of stimulation of sensitive or motor tissue structures, is perceived to be more pleasant and/or less tiring by patients when the stimulation effects of the individual stimulation current circuits do not run simultaneously but rather in cyclical turns, For example the effect is better physiologically and less tiring for the patient when electric stimulation therapy is used for muscle training and not only the "agonist", but also the "antagonist" are stimulated and vice versa, —not simultaneously, but in alternation: —first stimulating the agonist one or more times and then the antagonist one or more times, or vice versa, with the intensity of the stimulation of the agonist being adjustable to either the same or different intensity compared to the intensity of the stimulation of the antagonist. This last consideration also holds in general for the stimulation of other tissue structures.

The apparatus of the invention for electric stimulation equipment of the general kind under discussion provides for controlling the intensities of the electric stimulation currents in the individual stimulation current circuits in automatic alternation in such a way that the intensity of the stimulation effect at all times is more or less dominant in one or more current circuits in comparison to the intensity in the other current circuit or circuits. The intensity of the individual circuit current is automatically controlled in synchronism with a submultiple (division by a whole number) of the interference frequency, modulation frequency or contraction frequency in such a way that after one, two, three or n contractions of an agonist muscle there follows a sufficiently long rest pause during which the antagonist muscle is made to contract one, two, three or n times, and vice versa. Whereas in the use of this apparatus according to the invention in medium frequency therapy equipment, high voltage therapy equipment and low frequency or pulse current therapy equipment only one of the electric currents may be active in turn, while the others are to be completely devoid of current, yet in the case of interference current therapy equipment, the intensity of the currents of the current circuits are varied by only a certain amount with respect to each other, because otherwise no interference could arise.

BRIEF DESCRIPTION OF THE DRAWINGS

The invention is further described by way of illustrative example with reference to the annexed drawings, in which.

DESCRIPTION OF THE ILLUSTRATED EMBODIMENTS

Figure 1A:
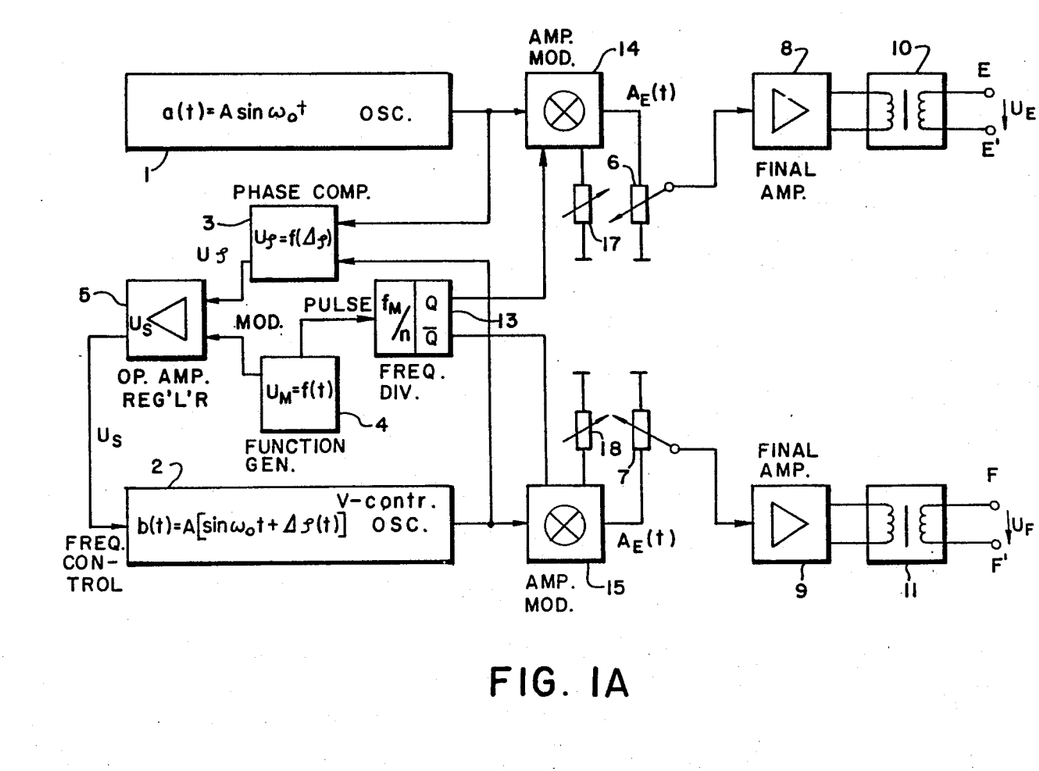
FIG. 1A is a schematic representation of apparatus, not including the electrodes to be applied to the patient which are shown in FIG. 1B according to the invention incorporated in an interference current therapy equipment.

FIG. 1A shows an embodiment apparatus according to the invention in another well known interference current therapy equipment. The interference current therapy equipment consists of an oscillator 1, which generates a sinusoidal voltage a(t) having the amplitude A and the frequency $f_o = \omega_o:2\pi$. This frequency is unregulated and does not need to be particularly constant. The second oscillator 2 as shown in FIG. 1 is automatically regulated to depend upon the frequency $f_o$. The oscillator 2 is a voltage controlled oscillator, the frequency of which can be made larger or smaller by the level of the control voltage $u_s$. The output signals of the two oscillators 1 and 2, which are in each case sinusoidal voltages, are compared in phase in a phase discriminator 3. This phase discriminator 3 delivers a voltage $u_\phi = f(\Delta\phi)$, proportional to the phase shift $\Delta\phi$ which is supplied to an operational amplifier 5 serving as a regulator and which is there compared with a phase modulation voltage $U_M = f(t)$, with the difference then being amplified in the operational amplifier 5 and supplied to the voltage controlled oscillator.

In this manner the frequencies of the two oscillators are synchronized with each other, although the output signal of the oscillator 2 is shifted in phase with respect to the output signal of the oscillator 1 by a phase angle that depends upon the phase modulation voltage $u_M$. If $u_M$ is constant over the time t, the phase shift $\Delta\phi$ is also constant over the time t. The principle of the interference current therapy equipment, as is known, involves periodic changing of the phase angle of the output voltage $U_F$ with respect to the output voltage $U_E$, these being the output voltages of the circuits E and F.

This takes place, for example, in such a way that the phase modulation voltage $u_M$ is changed periodically over the time t. It is in principle open to choice what time function the voltage $u_M$ follows. This time function may be varied at a constant period or with variable period duration.

The function generator 4, which generates phase modulation voltage $u_M = f(t)$ and delivers it to the operational amplifier-regulator 5 produces at the beginning or at the end of each period, regardless of whether the period duration of the periodic function $u_M = f(t)$ is constant or not, an electric pulse D which is supplied to a frequency divider 13 having the outputs Q and $\overline{Q}$. The division ratio of this frequency divider 13 is adjustable so that the logic level of the outputs Q and $\overline{Q}$ is switched over after every 1, 2, 3 ... or n pulses, where n can be any selected whole number, the switchover being either from logic level H to the logic level L or from L to H.

The output Q of the frequency divider 13 is supplied to the amplitude modulator 14 and the output $\overline{Q}$ is supplied to the amplitude modulator 15. The H logic level supplied alternately at the outputs Q and $\overline{Q}$ controls the respective amplitude modulators 14 and 15 respectively connected to Q and $\overline{Q}$ so that the amplitude of the voltages a(t) and b(t) are magnified or diminished, as the case may, by adjustable factors, respectively set at the adjusting devices 17 and 18 which are shown as potentiometers.

In this manner the amplitudes of the output voltages of the amplitude modulators 14 and 15 are correspondingly magnified or diminished in alternation at the frequency $f_M$: n by the factors set with the potentiometers 18 and 17 respectively.

Figure 1B:
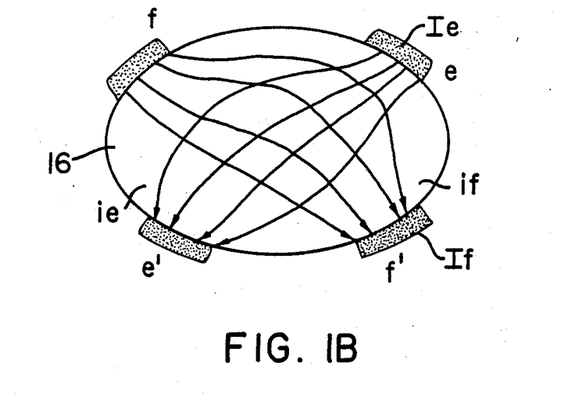

Before the output voltages $A_E(t)$ and $A_F(t)$ of the respective amplitude modulators 14 and 15 are respectively supplied to the final amplifiers 8 and 9, their amplitudes can be reduced, as may be desired or needed by means of the respective potentiometers 6 and 7. The outputs of the final amplifiers 8 and 9 are then supplied through the respective output transformers 10 and 11 to the output terminals E, E' in one case and F, F' in the other case. To these terminals there are connected respectively the electrodes e e' and f f' which are used to supply the respective currents $i_e$ and $i_f$ through the patient's biologic tissues 16 which are to be treated, as shown in FIG. 1B.

Figure 2A:
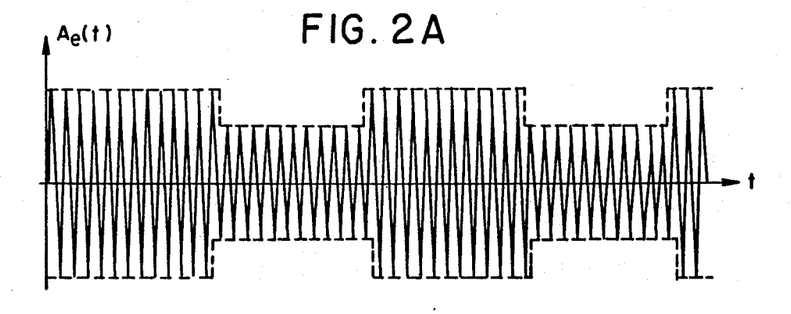
FIGS. 2A and 2B are diagrams of the alternatingly changing intensity of the respective stimulation currents in the current circuits E and F of an interference current therapy equipment according to FIGS. 1A and 1B and FIG. 2C shows phase shift to the same time scale as that of FIGS. 2A and 2B.
Figure 2B:
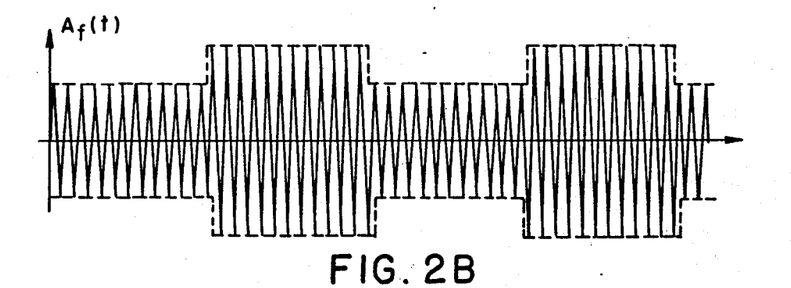
Figure 2C:
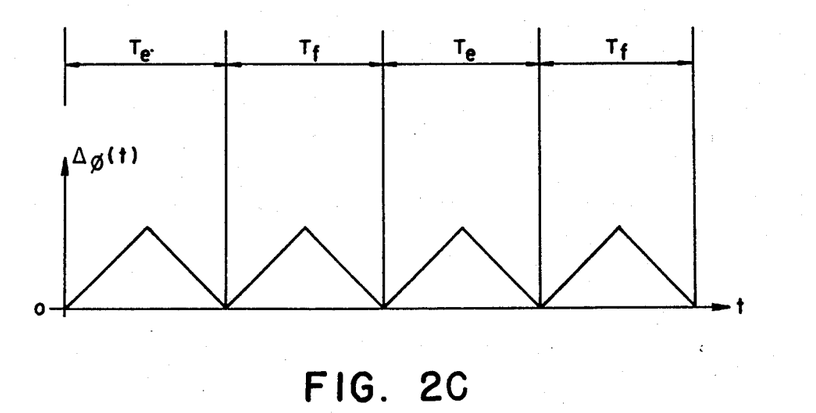

In FIGS. 2A and 2B the respective amplitudes $A_e(t)$ and $A_f(t)$ are shown schematically as parallel in time to the phase shift $\Delta\phi(t)$. Shown in FIG. 2C $\Delta\phi(t)$ is a function of $u_M(t)$. Every time that the phase angle $\Delta\phi$ passes through a defined value, for example whenever $\Delta\phi=0$, as shown in FIG. 2C, the function generator 4 supplies an electric pulse D to the frequency divider 13. At a division ratio of n=1 the amplitudes of $A_e$ and $A_f$ are alternatingly magnified and diminished, as shown in FIGS. 2A and 2B.

The electric pulses D, which are the delivered by the function generator 4 to the frequency divider 13 can, be initiated at any other phase angle $\Delta\phi$ between 0° and 180°, in which case the phase angle so defined must be taken into account only at increasing or at decreasing phase shifts, since otherwise the period duration $T_e$ will be different from the period duration $T_f$ and, besides, twice as many electric pulses D could be generated as in the case when the electric pulses D are generated at the 0 value or the maximum value of the phase angle $\Delta\phi$.

Figure 3A:
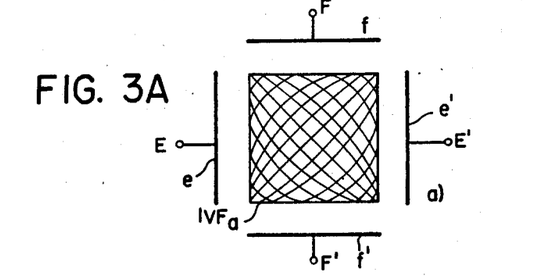
FIGS. 3A, 3B and 3C are schematic representations of the interference vector fields respectively for equal amplitude of both stimulation currents and for different amplitudes of for cases of the respective stimulation currents.
Figure 3B:
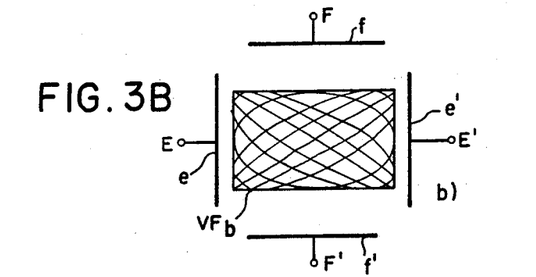
Figure 3C:
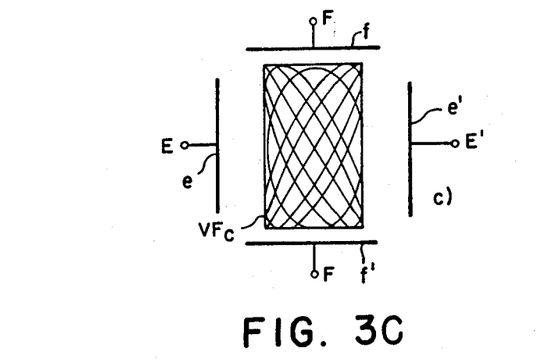

Three different interference vector fields are respectively shown in FIGS. 3A, 3B and 3C, strongly schematized. If the electrodes e, e', and f, f' are so applied to the living tissue to be treated that the electric fields and thereby the direction of the electric currents of the two stimulation current circuits EE', and FF' are thus at right angles, then in the case illustrated in FIG. 3A, where the amplitudes of the output voltages $U_E$ and $U_F$ are of the same magnitude, there occurs with continuous phase shift of the two output voltages, with respect to each other, from 0°–180°, a voltage or current vector field $VF_a$ that corresponds to a square.

If the amplitude of the output voltage $U_E$ at the electrodes ee' is greater than the amplitude of the output voltage $U_F$ at the electrodes ff', the voltage or vector field $VF_B$ in the shape of a rectangle having two long sides and two short sides is produced, as shown in the case shown in FIG. 3B.

In the case shown in FIG. 3C the output voltage $U_F$ at the electrodes ff' is greater than the output voltage $U_E$ at the electrodes ee'.

Figure 4A:
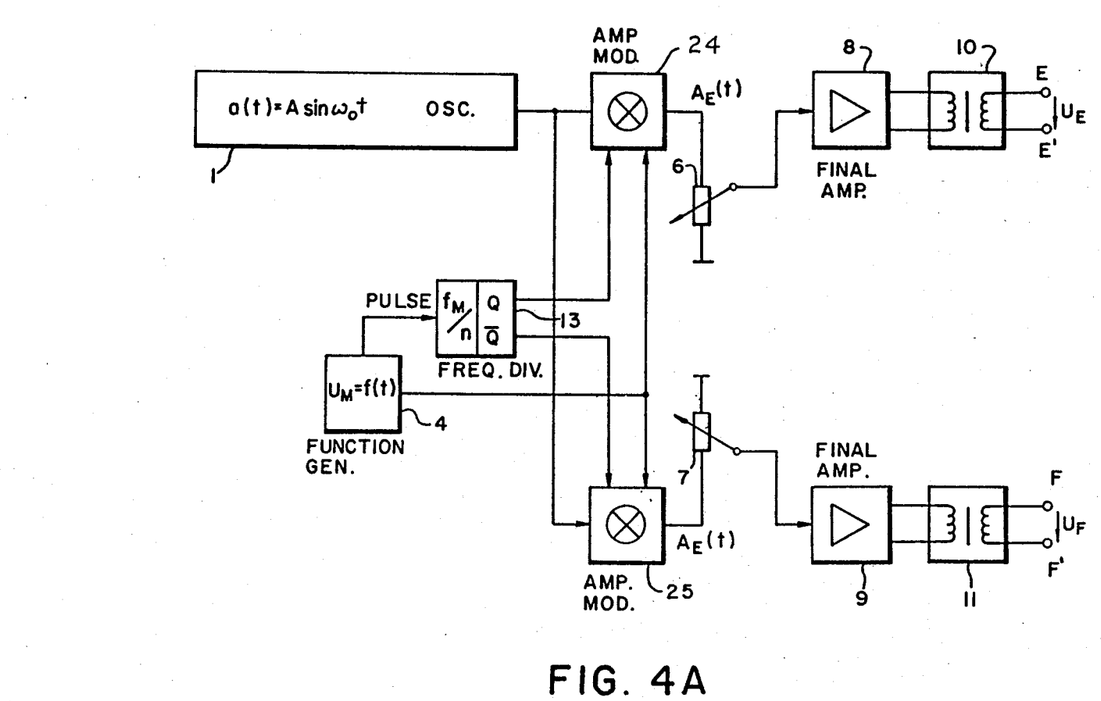
FIG. 4A is a schematic representation apparatus according to the invention in medium frequency therapy equipment not including the electrodes for the patent which are shown in FIG. 4B on the same sheet as FIG. 1B.
Figure 4B:
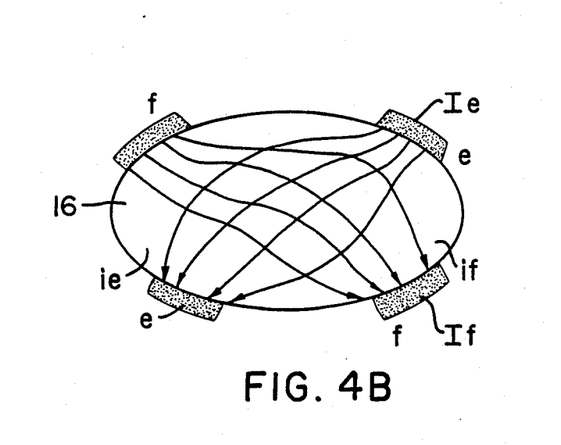

FIG. 4A and 4B show by way of example provision of the apparatus according to the invention in a so-called medium frequency electric therapy equipment.

A medium frequency electric therapy equipment applies medium frequency alternating currents with a frequency of a few kilohertz at both the outputs EE' and FF'. The amplitude of these alternating voltages is modulated by means of amplitude modulators 24 and 25 which are controlled by a function generator 4. The amplitude modulation of the two output voltages $U_E$ and $U_F$ is in full synchronism in the case of the known equipment. The improvement of such equipment by the present invention consists in that, just as in the case with the embodiment described in FIG. 1, there is not only the alternation described below but also the provision of electric pulses D of the function generator 4 which can be produced at the beginning or at the end of every period of the periodic function $u_M=f(t)$ which is a periodic but otherwise arbitrarily selectable function. For example a pulse D can be provided every time at the moment in which the modulation voltage $u_M=f(t)$ reaches a minimum. In this connection FIG. 5 also needs to be brought into consideration. The frequency divider 13 to which the electric pulses D are supplied operates in the manner above-described for the embodiment of FIG. 1. In contrast to the embodiment of FIGS. 1 and 2, however, the amplitude of the voltages $A_E(t)$ or $A_F(t)$ can be reduced alternately all the way down to 0 in this case.

Figure 5:
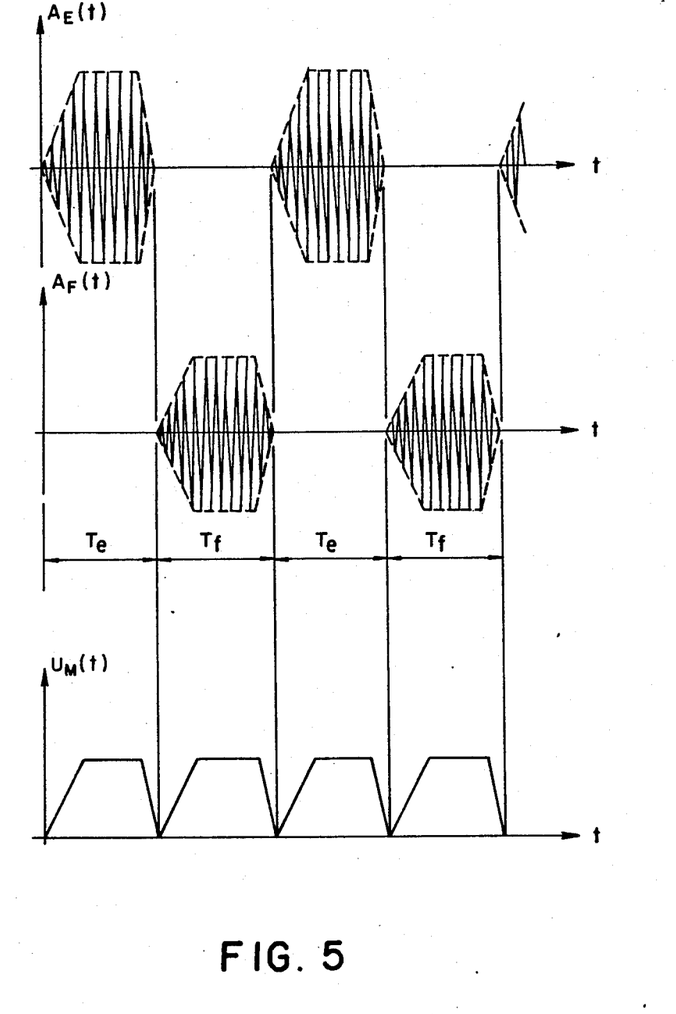
FIG. 5 is a diagram of the alternatingly changing intensity of the stimulation currents in the circuits E and F of the medium frequency therapy equipment according to FIG. 4.

This last-mentioned type of operation is schematically illustrated in FIG. 5. The modulation voltage $u_M(t)$ delivered by the function generator 4 runs in trapezonidal shape over the period t in the illustrated case. In consequence the amplitudes $A_E(t)$ and $A_F(t)$ are modulated trapezoidally over the period t. If the division factor n=1 is set at the frequency divider 13, there will then be provided, in alternation, a single period $A_E(t)$ while the amplitude $A_F(t)$ stays at zero, and then a single period $A_F(t)$ while the amplitude $A_E(t)$ is continuously at zero, and so on.

In the case of another division factor, for example n=3, there will be three periods each of the length $T_e$, and of non-zero values of the amplitude $A_e(t)$ produced while the amplitude $A_F(t)$ holds at zero, followed by three periods of non-zero values of $A_F(t)$, while $A_E(t)$ is at zero, and so on.

The amplitude of the output voltages $U_E$ and $U_F$ can, furthermore, be reduced independently of each other by means of the control potentiometers 6 and 7.

The periods of amplitude modulation designated $T_e$ and $T_f$, are equally long in periodic repetition of the function $U_M=f(t)$. The frequency $f_M$ means the number of periods of the modulation voltage $u_M=f(t)$ per unit of time.

The apparatus of the invention can also be used in a similar way in so-called high voltage equipment and pulse current equipment when at least two electric stimulation circuits are present which can be applied to a patient at the same time. In this case only the oscillator 1, which generates sinusoidal alternating current in FIGS. 1 and 4, is replaced with pulse generators and no output transformers should be inserted at the outputs of the two or more current circuits within the pulse current equipment.

Figure 8:
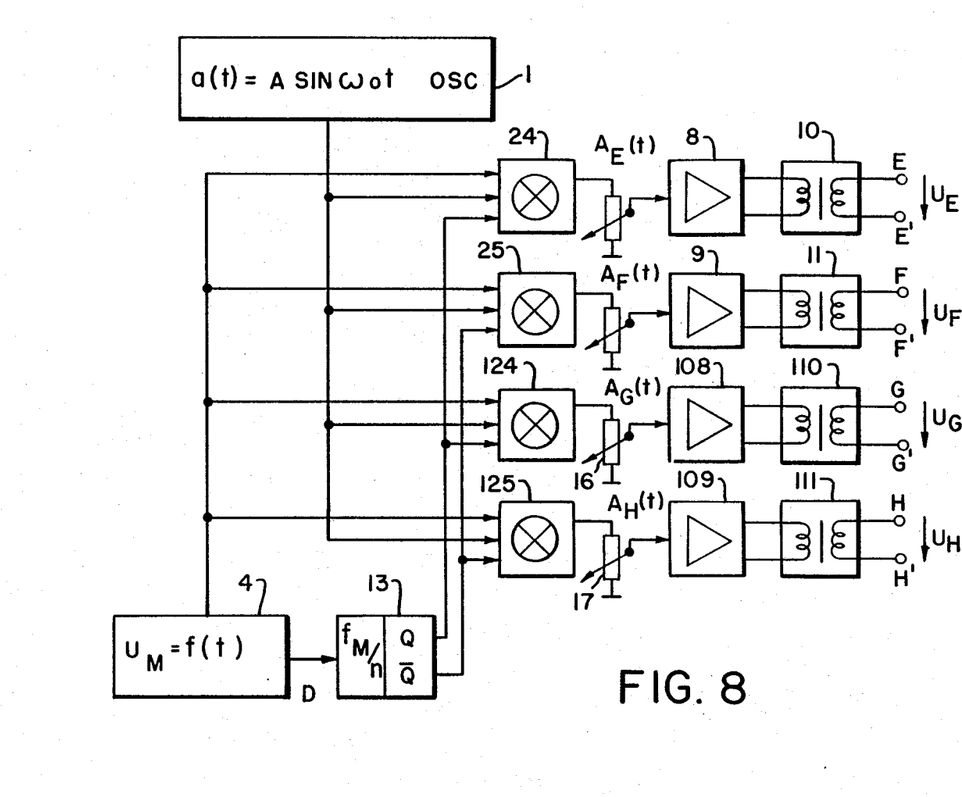
FIG. 8 is a circuit block diagram showing the use of a plurality of pairs of stimulation current circuits in an overall circuit of the kind shown in FIG. 4.

In a further development of the invention the number of stimulation current circuits can be doubled or further multiplied, in which case there are provided, in parallel to the illustrated to output circuits, identical additional circuits at the outputs of the amplitude modulators 14 and 15 or 24 and 25 (as shown in FIG. 8).

Figure 9:
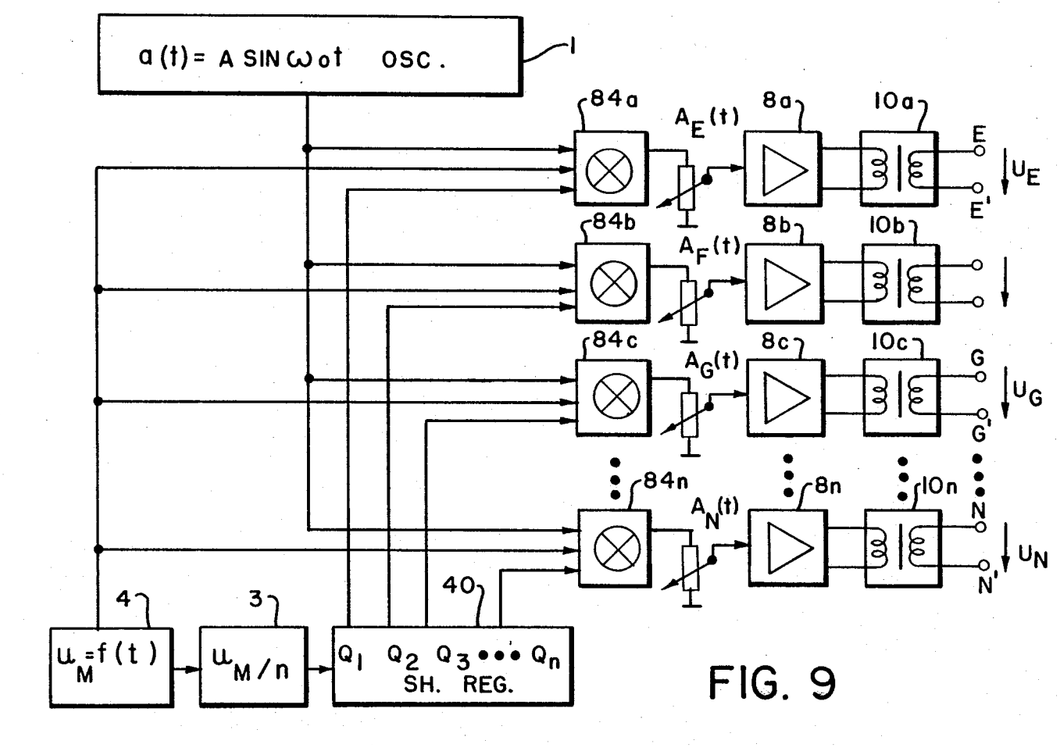
FIG. 9 is a circuit block diagram illustrating the use of a multiplicity of output circuits each energizing a stimulation circuit activated in sequence by a circuit of the kind shown in FIG. 7, for operation in a manner similar to that shown in FIG. 5.

Instead of the illustrated frequency divider 13 with only two outputs Q and $\overline{Q}$ a frequency divider with 3, 4 or more outputs could be used in which these outputs successively deliver a high voltage level for use in controlling a multiplicity of stimulation circuits in an arrangement illustrated in FIG. 9. For example a frequency divider with four outputs $Q_1$, $Q_2$, $Q_3$ and $Q_4$ will deliver high level voltage in succession first at $Q_1$, then at $Q_2$, then $Q_3$, then $Q_4$ and then again at $Q_1$ and so on, while the remaining outputs in each case are provided with a low level voltage. At each of these outputs a complete output circuit identical to the output circuit consisting of the elements 16, 6, 8 and 10 in FIG. 4 would be connected. In this manner several stimulation treatment runs can be coordinated in succession and performed cyclically for a patient.

Figure 6:
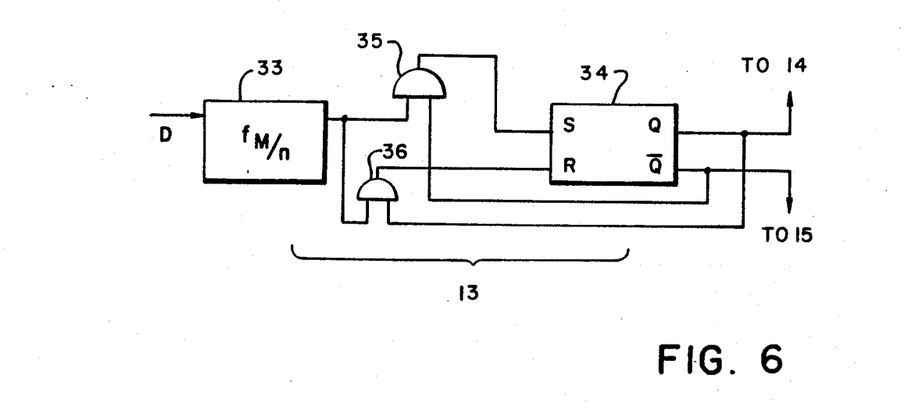
FIG. 6 is a logic circuit diagram of the output portion of the frequency divider 13 of FIGS. 1 and 4.
Figure 7:
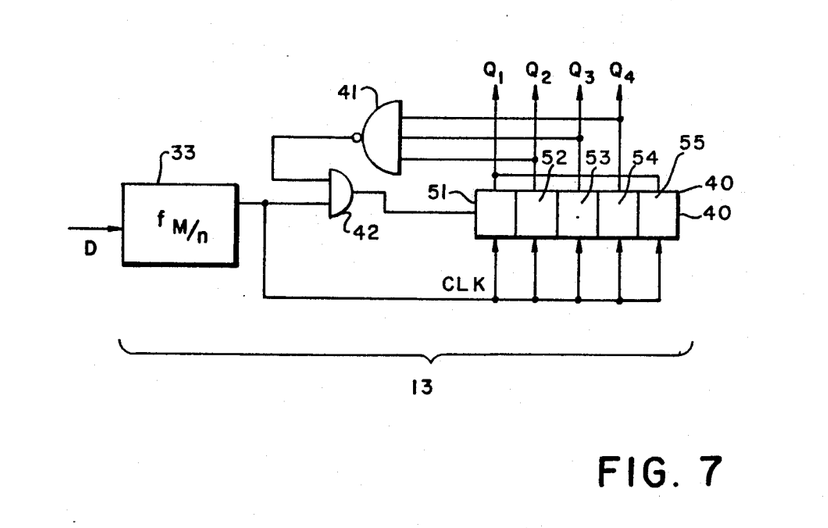
FIG. 7 shows a logic circuit diagram of a modified output portion of the frequency divider 13, for operation of more than two electric stimulation circuits in cyclical succession.

The difference in circuit logic between the output side of the frequency divider 13 having only two outputs Q and Q̄ and the kind of frequency divider just mentioned with four outputs $Q_1$, $Q_2$, $Q_3$ and $Q_4$ is illustrated with the logic circuits shown in FIGS. 6 and 7.

FIG. 6 shows a logic circuit for the output section of the unit described in FIGS. 1 and 4 as the frequency divider 13.

The left hand portion of the frequency divider 13 designated by a statement of the division operation it performs, namely $f_M/n$, is shown at 33 as a separate unit in FIGS. 6 and 7. It functions to count down the pulses D to provide an output at every pulse, every second pulse, every third pulse or any other selection of the division ratio. A simple counting circuit can be used. No attempt has been made to show the division ratio selection controls or circuits, since those are well known.

In FIG. 6 the alternation of outputs for the alternating control of two electric stimulation circuits is provided by the bistable stable circuit 34, which is shown in the conventional way with a set input S, a reset input R, a positive output Q and a negative output Q̄. The bistable circuit 34 is set and reset by alternate pulses from the output of the division circuit 33 by means of the two AND gates 35 and 36. When the bistable circuit 34 is in the reset state, the negative output Q̄ will be at a high logic voltage level and the next pulse from the divider 33 will set the circuit 34. Once the circuit is set, the positive output Q will have a high logic level voltage thus enabling the gate 36 to reset the circuit 34 when the following pulse comes from the division circuit 33. The precautions regarding operating time of the logic elements of the circuit which need to be considered for the stability of the operation of the circuit are well understood and do not need to be discussed here. The result is that two outputs in the circuit 34 alternate between high and low logic levels in opposite phase in step with the output pulses from the frequency division circuit 33.

In the circuit of FIG. 7, instead of the bistable circuit 34 a shift register 40 is used. For four outputs, in principle a 4-place shift register would be sufficient, but the first and last place operate simultaneously in FIG. 7 to assure stability in the particular logic circuit shown. When in the second, third and fourth cells there a state in which the respective outputs $Q_2$, $Q_3$ and $Q_4$ are of low logic level, the inverting input of the OR gate 41 is at a high level so that the arrival of a pulse from the frequency divider 33 finds the AND gate 42 ready to respond by producing a pulse at its output, which then produces a high level state in the first cell 51 of the shift register 40 and at its $Q_1$. All the output pulses of the frequency divider 33 are used to clock the shift register 40 through the clock line CLK, so that the next pulse will advance the content of the cell 51 to the cell 52, blocking the AND gate 42 and allowing the cell 51 to revert to the low output state. The high logic level content is then stepped on to the cells 53 and 54 by the next two pulses. Thereafter the next pulse finds the AND gate 42 enabled and puts the cell 51 again into the high level logic state. As already mentioned the cell 55 is not logically necessary, but may be useful to stabilize the circuit and assure that the output $Q_1$ will be as quickly changed as the others even though the loading of the cell 51 may be delayed by the operating time of the inverter in the output of the OR gate 41, for example.

There are many ways of implementing the logic circuits of FIGS. 6 and 7. For example, digital counters available on the market such as MC 1 4017 B from Motorola (USA) of HEF 4017 B from Valvo (BRD) could be used for alternating control of three or more output current circuits EE', FF' . . . and/or of related modulators (i.e. to perform the logic of FIGS. 7).

FIG. 8 is a simplified representation of the circuit of FIG. 4 modified for providing two pairs of stimulation circuits, with the members of both pairs being alternately switched simultaneously by the scale-of-two frequency divider 13.

The oscillator 1, the function generator 4 and the frequency divider 13, as well as the modulators 24 and 25, the final amplifiers 8 and 9 and the output transformers 10 and 11 are as shown in FIG. 4. There are added, in addition, another pair of modulators 124 and 125, another pair of output amplifiers 108 and 109 and another pair of output transformers 110 and 111.

FIG. 9 shows a circuit of the kind illustrated in FIG. 4 modified for energizing a multiplicity of stimulation circuits in sequence in the manner described above in connection with the description of FIG. 7. As in FIG. 7 the function generator 4 controls a frequency divider, in this case identified by the numeral 33, which controls the shift register 40 as in FIG. 7, the shift register being shown in this case for operating a number of output circuits greater than 4. The oscillator 1 makes high frequency electric voltage and current available to the respective modulators 84a, 84b, 84c . . . 84n. The modulated high frequency energy is amplified in respective final amplifiers 8a, 8b, 8c . . . 8n and then supplied through respective output transformers 10a, 10b, 10c . . . 10n to output terminals E, E'; F, F'; G, G' . . . N, N' which are connectable to stimulation circuits, in each case to a pair of electrodes, in the same way as the output terminal E, E' in FIG. 1 and FIG. 4.

Although the invention has been described with reference to particular illustrative examples, it will be understood that further modifications and variations are possible within the inventive concept.

I claim:

1. An electric stimulation therapy equipment having a plurality of electric stimulation circuits for connection to the body of a patient, said equipment having means for generating electric oscillations in alternating voltage or pulse form and being an equipment of the group consisting of interference stimulation therapy equipment having means for generating said oscillations in alternating current form and having means for differentially phase modulating said oscillations periodically at low frequency for at least a pair of said stimulation circuits, medium frequency alternating current therapy equipment having means for generating electric oscillations in alternating current form and means for low frequency periodic modulation in phase or amplitude of said alternating current oscillations for said electric stimulation circuits and medium frequency pulse current therapy equipment having means for generating electric oscillations in pulse form and having means for low frequency periodic modulation in phase, width or amplitude of pulse form oscillations for said electric stimulation circuits, said equipment further comprising apparatus for output control including:

a function generator (4) having a first output at which a periodic-cycle low frequency modulating voltage ($u_M$) is generated for modulating said oscillations of said generating means and a second output at which a pulse is made available at a defined time of each cycle period of said modulating voltage;

adjustable frequency division means (13) for division of the frequency of pulses of said second output of said function generator by a selectable whole number 1, 2, 3 ... n and for supplying high and low output level control voltages in different alternations at least two control outputs, which alternations are switched by frequency divided pulses generated within said frequency-division means;

a plurality of amplitude modulators (14, 15) respectively for the circuits of at least two of said electric stimulation circuits, said modulators having first inputs connected to said electric oscillation generating means and having control inputs respectively connected to said at least two control outputs of said adjustable frequency division means, and a plurality of amplitude modulation adjustment means (17, 18) for respectively applying factors for raising or lowering the amount of amplitude modulation respectively produced in said plurality of amplitude modulators by said respective outputs of said at least two control outputs of said adjustable frequency division means.

2. Apparatus according to claim 1, wherein said adjustable frequency division means (13) has a single pair of control outputs at which said high and low output level control voltages are supplied in opposite alternations, wherein said plurality of amplitude modulators (14, 15) consists of first and second amplitude modulators respectively for the circuits of a pair of said electric stimulation circuits, said modulators having control inputs respectively connected to said pair of control outputs of said adjustable frequency division means, and wherein said plurality of amplitude modulation adjustment means (17, 18) consists of first and second amplitude modulation adjustment means for respectively applying factors for raising or lowering the amount of amplitude modulation respectively produced in said first and second amplitude modulators.

3. Apparatus according to claim 2, wherein said first and second amplitude modulators, said first and second amplitude modulation adjustment means, and also first and second final amplifying and coupling means which are respectively provided for connecting the outputs of said first and second amplitude modulators and amplitude modulation adjustment means to make suitable contact with a patient through contact electrodes respectively constitute first and second electric stimulation circuits for connection to the body of said patient, and wherein at least one additional pair of electric stimulation circuits is provided in said equipment likewise including in each additional pair of circuits first and second amplitude modulators, first and second amplitude modulation adjustment means for output control, as well as first and second final stage amplifying and coupling means, said additional first and second amplitude modulators likewise having first inputs connected to said electric oscillation generating means and likewise having control inputs respectively connected to said pair of control outputs of said adjustable frequency division means, whereby a plurality of pairs of said electric stimulation circuits of said equipment and apparatus may be operated in parallel.

4. Apparatus according to claim 3, wherein said electric stimulation therapy equipment is a said interference stimulation therapy equipment, wherein said means for differentially phase modulating said oscillations generated by said oscillation generating means periodically at low frequency is a phase modulator having a control input connected to said first input of said function generator and an output connected to an auxiliary oscillation generator of said electric oscillation generating means which is additional to a main generator of said electric oscillation generating means, and wherein said first and second amplitude modulators have their respective first inputs connected respectively to said main and auxiliary oscillation generators of said electric oscillation generating means.

5. Apparatus according to claim 3, wherein said equipment is an equipment of the group consisting of medium frequency alternating current therapy equipment having means for generating electric oscillations in alternating current form and means for low frequency periodic amplitude modulation of said alternating current oscillations for said electric stimulation circuits and medium frequency pulse current therapy equipment having means for generating electric oscillations in pulse form and having means for low frequency periodic amplitude modulation of pulse form oscillations for said electric stimulation circuits, and wherein:

said plurality of amplitude modulators constitute said means for low frequency periodic amplitude modulation of said oscillations, having their first inputs connected to said means for generating electric oscillations, and each has a first and a second control input;

said function generator has its first output connected to all said first control inputs of said respective amplitude modulators, and said frequency division means has its said control outputs respectively connected to said second control inputs of said respective amplitude modulators.

6. Apparatus according to claim 2, wherein said electric stimulation therapy equipment is a said interference stimulation therapy equipment, wherein said means for differentially phase modulating said oscillations generated by said oscillation generating means periodically at low frequency in a phase modulator having a control input connected to said first input of said function generator and an output connected to an auxiliary oscillation generator of said electric oscillation generating means which is additional to a main generator of said electric oscillation generating means, and wherein said first and second amplitude modulators have their respective first inputs connected respectively to said main and auxiliary oscillation generators of said electric oscillation generating means.

7. Apparatus according to claim 2, wherein said equipment is an equipment of the group consisting of medium frequency alternating current therapy equipment having means for generating electric oscillations in alternating current form and means for low frequency periodic modulation in phase or amplitude of said alternating current oscillations for said electric stimulation circuits and medium frequency pulse current therapy equipment having means for generating electric oscillations in pulse form and having means for low frequency periodic amplitude modulation of pulse form oscillations for said electric stimulation circuits, and wherein:

said plurality of amplitude modulators constitute said means for low frequency periodic amplitude modulation of said oscillations, having their first inputs connected to said means for generating electric oscillations, and each has a first and a second control input;

said function generator has its first output connected to all said first control inputs of said respective amplitude modulators, and said frequency division means has its said control outputs respectively connected to said second control inputs of said respective amplitude modulators.

8. Apparatus as defined in claim 1, wherein at least three electric stimulation circuits are provided for connection to the body of said patient and said plurality of amplitude modulators comprises at least three amplitude modulators respectively for said at least three electric stimulation circuits, each of said amplitude modulators having a first input connected to said electric oscillation generating means, and said adjustable frequency division means (13) having at least three outputs respectively corresponding to said at least three electric stimulation circuits and said at least three amplitude modulators and respectively connected to said control inputs of said amplitude modulators, and means in said frequency division means for cyclically supplying a said high output control voltage to each of said at least three outputs cyclically in turn while supplying said low output control voltages to those of said at least three outputs to which said high output control voltage is not supplied.

9. Apparatus according to claim 8, wherein said equipment is an equipment of the group consisting of medium frequency alternating current therapy equipment having means for generating electric oscillations in alternating current form and means for low frequency periodic amplitude modulation of said alternating current oscillations for said electric stimulation circuits and medium frequency pulse current therapy equipment having means for generating electric oscillations in pulse form and having means for low frequency periodic amplitude modulation of pulse form oscillations for said electric stimulation circuits, and wherein:

said plurality of amplitude modulators constitute said means for low frequency periodic amplitude modulation of said oscillations, having their first inputs connected to said means for generating electric oscillations, and each has a first and a second control input;

said function generator has its first output connected to all said first control inputs of said respective amplitude modulators, and said frequency division means has its said control outputs respectively connected to said second control inputs of said respective amplitude modulators.

10. Apparatus according to claim 1, wherein said equipment is an equipment of the group consisting of medium frequency alternating current therapy equipment, having means for generating electric oscillations in alternating current form and means for low frequency periodic amplitude modulation of said alternating current oscillations for said electric stimulation circuits, and medium frequency pulse current therapy equipment having means for generating electric oscillations in pulse form and having means for low frequency periodic amplitude modulation of pulse form oscillations for said electric stimulation circuits, and wherein:

said plurality of amplitude modulators constitute said means for low frequency periodic amplitude modulation of said oscillations, having their first inputs connected to said means for generating electric oscillations, and each has a first and a second control input;

said function generator has its first output connected to all said first control inputs of said respective amplitude modulators, and said frequency division means has its said control outputs respectively connected to said second control inputs of said respective amplitude modulators.

* * * * *